United States Patent [19]
Klearman et al.

[11] Patent Number: 5,472,421
[45] Date of Patent: * Dec. 5, 1995

[54] PILL CRUSHING SYRINGE WITH PLUG TO IMPEDE CRUSHED PILL PARTICLES FROM PREMATURELY ENTERING THE CATHETER

[75] Inventors: Jeffrey D. Klearman; Matt Roth, both of St. Louis; Jerry Roth, House Springs; Robert Bronson, St. Louis, all of Mo.

[73] Assignee: Lake Medical Products, Inc., St. Louis, Mo.

[*] Notice: The portion of the term of this patent subsequent to Dec. 27, 2011, has been disclaimed.

[21] Appl. No.: 354,677

[22] Filed: Dec. 13, 1994

Related U.S. Application Data

[63] Continuation-in-part of Ser. No. 264,628, Jun. 23, 1994, which is a continuation-in-part of Ser. No. 168,019, Dec. 15, 1993, Pat. No. 5,376,072.

[51] Int. Cl.$^6$ .................................................. A61M 37/00
[52] U.S. Cl. ................................ 604/82; 604/56; 604/92; 604/218
[58] Field of Search ................................. 604/56, 82–83, 604/92, 187, 191, 211, 222, 218, 224, 225, 57, 77–79, 84–85

[56] References Cited

U.S. PATENT DOCUMENTS

| | | |
|---|---|---|
| 1,165,686 | 12/1915 | McElroy . |
| 2,392,595 | 6/1959 | Tupper . |
| 2,602,596 | 7/1952 | Jones et al. . |
| 3,915,393 | 10/1975 | Elkins . |

(List continued on next page.)

OTHER PUBLICATIONS

American Medical Industries brochure entitled "Making Yor Medications & Vitamins EZ to Swallow", including enclosure entitled Remembering Your Medication Schedule is EZ.

American Medical Industries sales flier entitled "Welcome to American Medical Industries" Family of EZ-Health™

(List continued on next page.)

Primary Examiner—C. Fred Rosenbaum
Assistant Examiner—Perry E. Van Over
Attorney, Agent, or Firm—Rogers, Howell & Haferkamp

[57] ABSTRACT

A pill crushing syringe is disclosed which includes a barrel and a plunger, with abraded surfaces on each so that a pill placed in the barrel is crushed as the plunger advances within the barrel. The barrel has an aperture located near the closed end with a catheter connected around and extending from the aperture. The plunger has a sealing gland to provide an airtight seal with the barrel so that liquid may be drawn into the barrel through the aperture by withdrawing the plunger from the barrel to thereby suspend the crushed pill in the liquid, and the suspension may be flushed from the barrel by thereafter advancing the plunger into the barrel. In an alternative embodiment, a bi-level barrel has an aperture in spaced relation to the closed end forming a pocket wherein the crushed pill ingredients accumulate. The pocket at the closed end and the separation between the aperture and the barrel closed end helps prevent the medication from escaping the barrel via the catheter prior to aspiration. In still other embodiments, the syringe has a side entry plunger or two opposing plungers. In a further alternative embodiment, the aperture extends through the otherwise closed second barrel end and the catheter extends axially therefrom in better visual conformity with typical syringes. The abraded surfaces include radial protrusion patterns and a plug extending from the plunger prevents the abraded surfaces from meshing to thereby reduce packing of the pill particles between the abraded surfaces. The plug also blocks the catheter when the plunger is fully advanced into the barrel to prevent the medication from escaping via the catheter prior to aspiration.

36 Claims, 8 Drawing Sheets

U.S. PATENT DOCUMENTS 4,057,052  11/1977  Kaufman et al. .
4,209,136   6/1980  Linden et al. .
4,366,930   1/1983  Trombetti, Jr. .
4,568,331   2/1986  Fischer et al. .
4,715,854  12/1987  Vaillancourt .
4,765,549   8/1988  Sherman .
5,067,666  11/1991  Sussman .
5,118,021   6/1992  Fiocchi .
5,148,995   9/1992  Hurst .

OTHER PUBLICATIONS

Products, 1993.

American Medical Industries Facsimile transmission to Lake Medical Products, Inc. regarding EZ Swallow Pill Crushers & Pill Splitters, Sep. 1, 1993.

Gerber Products Company, Baby Medi–Spoon, 1991.

5,472,421

PILL CRUSHING SYRINGE WITH PLUG TO IMPEDE CRUSHED PILL PARTICLES FROM PREMATURELY ENTERING THE CATHETER

CROSS-REFERENCE TO RELATED APPLICATION

This application is a continuation-in-part of Ser. No. 08/264,628, filed Jun. 23, 1994, which is a continuation-in-part of Ser. No. 08/168,019, filed Dec. 15, 1993, now U.S. Pat. No. 5,376,072, the disclosures of which are incorporated herein.

FIELD OF THE INVENTION

This invention relates to an apparatus for, and method of, crushing a pill, mixing the resulting powder with a liquid and administering the suspension.

BACKGROUND AND SUMMARY OF THE INVENTION

In many instances, it is difficult if not impossible to administer medication in capsule form to patients. This is particularly true for patients who may be comatose or otherwise physically unable to swallow the pills. For those people, in the prior art, the pills were ground with a mortar and pestle. The powder was transferred to a liquid-filled container and mixed with the liquid. The suspension was then either swallowed, or a syringe was filled with the suspension and injected into an intravenous tube or other tube generally used in hospital settings.

The prior art technique carried several drawbacks. The most serious of these were the risks of low and unpredictable compliance and cross-contamination. As the pill was crushed in a mortar and then transferred to another container before being administered, a nurse using extreme care could not help but lose some of the pill as residue on the mortar, pestle, etc. Furthermore, this residue would necessarily vary both in quantity and content from dose to dose to thereby perhaps alter the dosage administered from that intended. In extreme situations, this could interfere with achieving the desired medical result.

The undesired, but inescapable, residue also created an unavoidable risk of cross-contamination as the same mortar and pestle were typically re-used for the same and other patients; as well.

Moreover, the prior art technique was very time consuming as the nurse needed to use care and caution to avoid spillage, which translated into increased nurse or medical technician time and expense.

Other pill crushing devices are also known in the prior art. However, similar to the mortar and pestle technique discussed above, these devices were designed to grind or crush the pill in one compartment, transfer the powder to another liquid-filled container where the powder was dissolved or suspended and then administered. These devices similarly carried the risks of contamination, cross-contamination, spillage and waste, and were again time consuming.

The invention disclosed in the parent hereto, as cross-referenced above, overcomes the foregoing problems by providing a pill crushing syringe which is adapted to crush medication, preferably a pill, and mix the resulting powder with liquid all within the syringe itself, and then administer the suspension with the same syringe. Generally the syringe disclosed in the parent includes a barrel and a plunger. The syringe has two opposing abraded surfaces, one on the plunger and one in the barrel bottom, to crush a pill placed in the barrel by the plunger as it is advanced to the bottom of the barrel. The pill could even be "ground" by rotating the plunger within the barrel to achieve a complete breakdown of the pill into small and regularly sized particles. In an alternate embodiment of the invention disclosed in the parent, the bottom of the barrel may be threaded so that it may also be rotated, thereby permitting both abraded surfaces to be positively driven with respect to each other. The barrel includes an aperture and a catheter located at the bottom of the barrel for drawing liquid into the barrel to mix with the crushed pill particles. The plunger includes a sealing gland providing an airtight relationship between the plunger and the barrel to assist in drawing liquid into the barrel by withdrawing the plunger from the barrel when the catheter tip is submerged in the liquid. The suspension of the liquid and crushed pill particles is administered by advancing the plunger into the barrel thereby forcing the suspension through the catheter and into a tube attached to the patient.

Generally, the method of the invention disclosed in the parent comprises providing a pill crushing syringe including a barrel and a plunger with opposing abraded surfaces so that medication, preferably a pill, placed in the barrel is crushed as the plunger is "bottomed" within the barrel, placing a pill into the barrel, crushing the pill, adding liquid to the barrel thereby suspending the powder in the liquid, and flushing the suspension.

The apparatus and method of the parent invention are significant improvements over the prior art in that pills are crushed, the resulting powder mixed with liquid, and the suspension administered all with the same syringe. Because the pill is crushed in a closed container and the powder need not be transferred for mixing with the liquid, the risk of cross-contamination and spillage is greatly reduced while consistency of compliance is achieved. Moreover, the abraded surfaces used to crush the pills are exposed to the liquid drawn into the barrel which provides a "washing" action on the very surfaces used to grind the pill. This helps to minimize residue.

In addition to reducing the risk of waste and contamination, insuring a high dosage compliance rate, and eliminating the problem of cleaning the pestle and mortar, the invention disclosed in the parent saves nurses time allowing more medicinal dosages to be administered within the same time frame in a reliable manner. Further, the syringe may be made of plastic and used only once, thereby eliminating the risk of cross-contamination.

As disclosed in the continuation-in-part application of the parent disclosed above, Ser. No. 08/264,628, filed Jun. 23, 1994, the inventors have improved their earlier pill crushing syringe by providing a bi-level barrel having an open end, a closed end and a cylindrical wall, and a mating bi-level plunger having a tip end. As in the parent, the syringe has two opposing abraded surfaces, one on the plunger tip end and one on the barrel closed end to thereby crush a pill placed in the barrel as the plunger is advanced and rotated within the barrel. The present invention further includes an aperture through the barrel wall in spaced relation to the closed barrel end such that a pocket is formed by the barrel wall and the closed end between the aperture and the closed end. A substantially straight catheter is connected around and extends from the aperture. By holding the syringe upright, the crushed pill ingredients remain in this pocket prior to aspiration, thereby assuring high dosage integrity by prohibiting medication from escaping through the catheter.

In the parent, the preferred location of the aperture is adjacent the barrel closed end, and a "crooked" catheter is preferred to assure no medication escapes prior to aspiration. The "crooked" catheter arrangement provides quite favorable results. However, the pocket between the aperture and the barrel closed end of the present invention attains equally favorable dosage integrity while allowing the use of a substantially straight catheter. The straight catheter design is better suited for present injection molding technology and thus is significantly less expensive to manufacture.

An alternative means for crushing the pill into a powder provides a bi-level barrel and a bi-level plunger, wherein the barrel further includes a side opening with a hollow side arm extending from the side opening. A reinforced barrel wall section having an interior abraded surface is positioned opposite the side opening. A side entry plunger having an abraded tip end is movable within the side arm and the side entry plunger is adapted to engage the reinforced wall abraded surface as the side entry plunger advances within the hollow arm and into the barrel. A pill placed between the reinforced wall abraded surface and the side entry plunger abraded tip end is crushed as the side entry plunger is advanced into and rotated within the barrel.

Another alternative embodiment provides a cylinder with two plungers having opposing abraded tip ends adapted to crush a pill placed therebetween by advancing the plungers within the cylinder and rotating the plungers in opposite directions. A catheter is connected around and extends from an aperture through the cylinder wall. A space between the two plungers, which encompasses the crushed pill ingredients, may be positioned to be in fluid connection with the aperture thereby allowing aspiration of the pill ingredients.

Building on the invention disclosed above, the inventors herein have improved their earlier designs by providing a pill crushing syringe which is more economical to manufacture, has very favorable pill crushing and dosage compliance characteristics, and minimizes fluid residue within the syringe. Moreover, the syringe of the present invention is in closer visual conformity with typical syringes used in the health care field which minimizes operator apprehension commonly experienced when first using a new product. As in the parent, the syringe includes a barrel having a first open end, a generally closed second end, and a cylindrical wall therebetween as well as a plunger movable within the barrel. The syringe has two coaxially aligned opposing abraded surfaces, one on a tip end of the plunger and one on the second barrel end to thereby crush a pill placed in the barrel as the plunger is advanced and rotated within the barrel.

The present invention further includes an aperture near the center of the second barrel end and a substantially straight catheter extending from the aperture which visually resembles typical syringes. The plunger tip is conically shaped, the barrel second end is frustoconically shaped (because of the aperture through the center thereof), and each has an abraded surface of a protrusion pattern comprising a radially extending, alternating pattern of ridges and valleys. A plug extends from the center of the plunger tip and is sized to prevent the opposing abraded surfaces from meshing which minimizes packing of the pill crushings within the valleys. By holding the syringe in its inverted vertical orientation while crushing the pill, the pill (and resulting pill particles) gravitate radially outwardly and downwardly along the conic plunger tip, principally following the valleys, and away from the aperture.

The radially extending protrusion pattern on the coaxially aligned opposing abraded surfaces provides a number of advantages over the pyramid-shaped protrusions arranged in a grid of intersecting lines and columns shown in the parent and continuation-in-part hereto. While the plug extending from the plunger tip prevents the opposing abraded surfaces from meshing, the ridges of the opposing abraded surfaces make contact and partially wipe each other when the plunger is rotated within the barrel. This partial wiping action helps remove any pill crushings which might otherwise be matted against the opposing ridges and creates a vibrating reciprocating action with the abraded surfaces as the plunger is rotated which facilitates a more complete crushing of the pill. The present invention reliably aligns the opposing ridges and valleys and reliably regulates the amount of wiping and the degree of vibrating reciprocation by assuring that two physical characteristics of the syringe are within tolerance: coaxial alignment of the abraded surfaces and the plug length.

There is no teaching of reliable alignment, or regulating the wiping and vibrating reciprocation with the prior art pill crushing abraded surfaces. Each prior art abraded surface typically contains 45 pyramids. Because the location, height, and width of 90 pyramids (45 on each abraded surface) must be individually accounted for, alignment is difficult to precisely control. Moreover, seating, the degree of vibrating reciprocation, and the precise portion of each pyramid which wipes opposing pyramids is difficult to measure and even more difficult to reliably repeat. Production of one or more of the pyramids out of tolerance (too fat, too tall, etc.) may significantly alter the pill crushing characteristics of those abraded surfaces. Perhaps more importantly, as the pyramid abraded surfaces are typically individually mounted to the pill crushing device after their separate manufacture, it is very difficult to maintain alignment of these separate surfaces. Thus, the radial protrusion pattern of the present invention provides functional advantages over the prior art in that alignment of opposing ridges and valleys and pill crushing characteristics are predictable and reliably repeatable by closely controlling only two of the syringe's physical dimensions (coaxial alignment of the abraded surfaces and the plug length) thereby enabling economic mass production of the pill crushing syringe.

When the pill is sufficiently crushed, the plunger is advanced fully into the barrel which forces the plug to block the catheter passage. With the catheter passage blocked, the syringe may be tilted downward and the catheter submerged in preparation for aspiration with minimal risk of the medication prematurely gravitating into the catheter. With this method, the pill crushings not only gravitate to the outer circumference of the plunger/barrel and away from the aperture when the syringe is vertically inverted, but the plug also physically blocks the aperture to prevent their escape. By preventing the opposing abraded surfaces from meshing, the plug also minimizes packing of the pill ingredients between the ridges and valleys allowing the pill particles to quickly and more completely dissolve during aspiration.

In the parent, the abraded surfaces are shown as orthogonal to the barrel and plunger axes and include a plurality of pyramid-shaped protrusions arranged in a grid of intersecting lines and columns. The location of the aperture in the parent is adjacent the barrel second end and a "crooked" catheter is utilized to assure no medication escapes prior to aspiration. The orthogonal, grid-like abraded surface pattern, and "crooked" catheter arrangement provide quite favorable results. However, centrally locating the catheter in the second barrel end (as opposed to the side) and utilizing a radial abraded surface pattern comprised of continuous ridges and valleys results in a design better suited for present injection molding technology and thus significantly less expensive to manufacture. Moreover, the radial protrusion pattern produces superb crushing results and, as explained above, the plug of the present invention assures a high degree of dosage integrity. The frustoconic shape of the barrel closed end minimizes any residual liquid within the syringe further contributing to the high-dosage compliance obtained by the present invention. Furthermore, because the present invention more closely resembles traditional syringes, health care personnel will be more receptive to the familiar style and less apprehensive when initially using the syringe.

DETAILED DESCRIPTION OF THE PREFERRED EMBODIMENT

Figure 1:
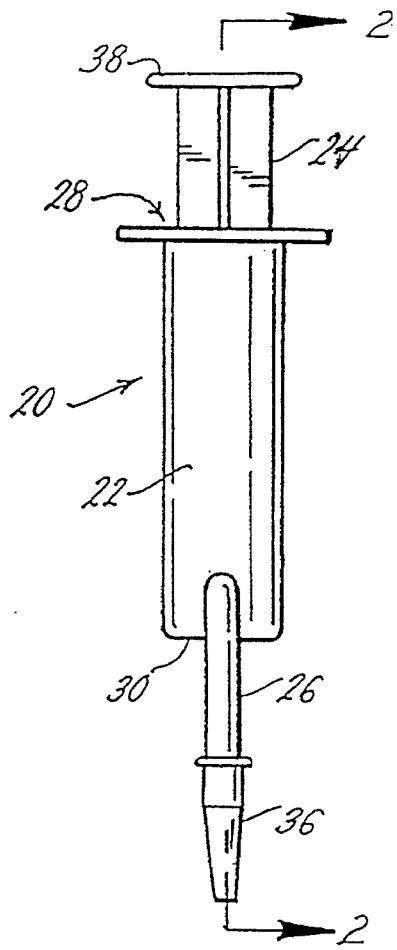
FIG. 1 is an elevation view of the pill crushing syringe constructed according to the principles of the invention disclosed in the parent.
Figure 3:
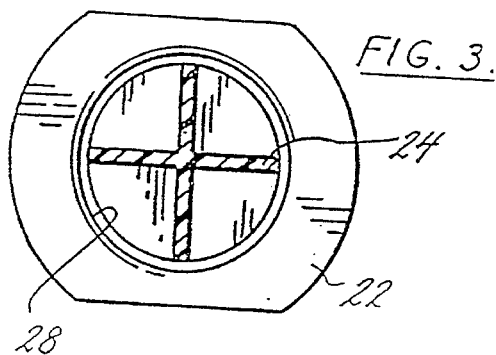
FIG. 3 is a cross-sectional view taken along lines 3—3 in FIG. 2 detailing the construction of the plunger disclosed in the parent.

A pill crushing syringe constructed according to the principles of the invention disclosed in the parent is indicated generally as 20 in FIG. 1. The syringe includes a barrel 22, a plunger 24, and a catheter 26.

Figure 4:
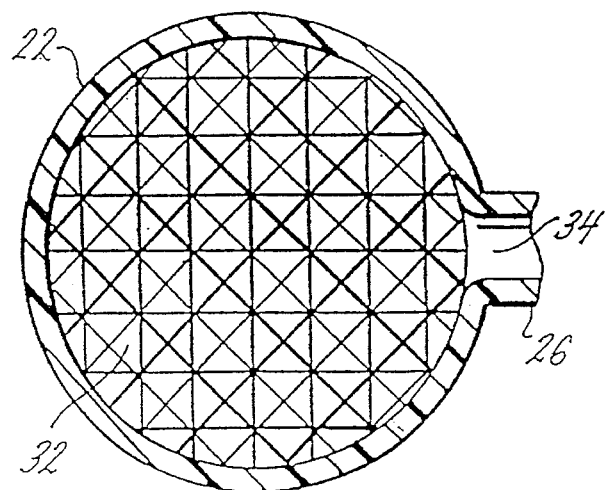
FIG. 4 is a cross-sectional view taken along lines 4—4 in FIG. 2 detailing the construction of the abraded surface.
Figure 2:
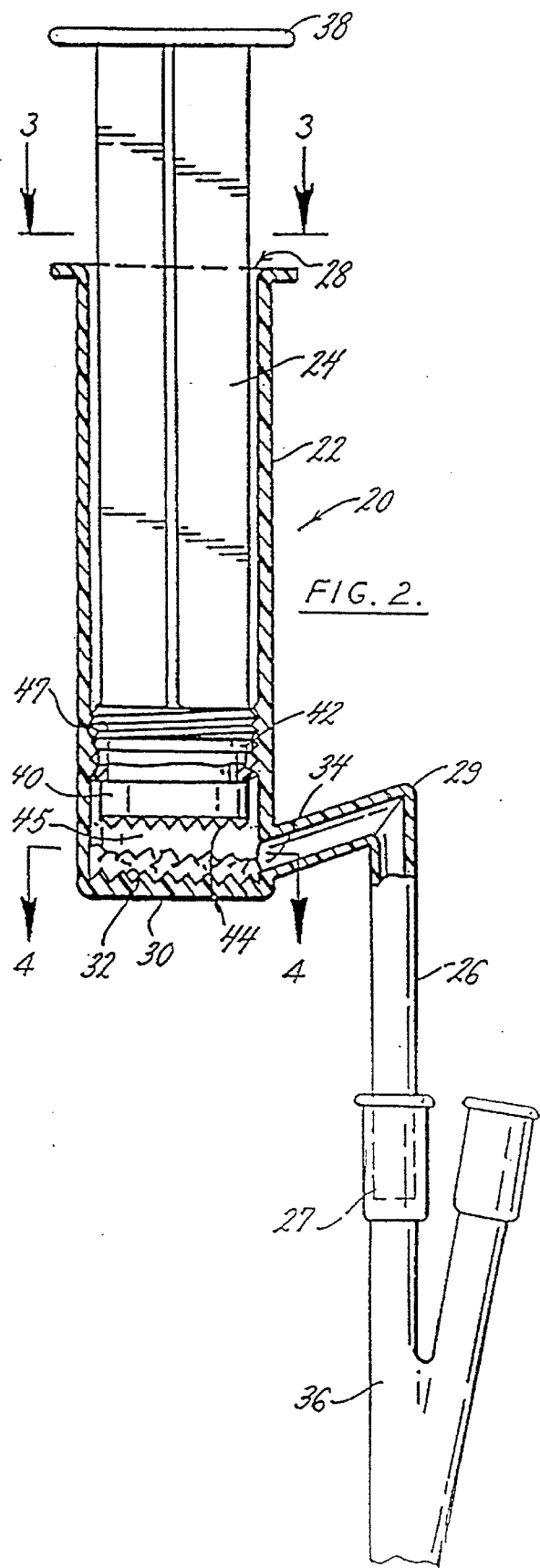
FIG. 2 is a cross-sectional view taken along lines 2—2 in FIG. 1 detailing the interior construction of the syringe disclosed in the parent.

The barrel 22 includes an open end 28 and a preferably flat closed end 30. The closed end 30 has an interior abraded surface 32 which is shown in FIGS. 2 and 4 as preferably serrated. An aperture 34 is formed through the barrel wall preferably adjacent to the abraded surface 32, and the catheter 26 is connected around and extends from aperture 34. The catheter 26 is shown in FIG. 2 as preferably having a crook 29 and including a tip 27 for insertion into a tube 36. In the preferred embodiment, the tube 36 is one commonly used in hospital settings, such as a nasal-gastric tube, gastrostomy tube or a jejunostomy tube, for example.

The plunger 24 includes a handle end 38, a tip end 40, and a sealing gland 42 providing an airtight relationship between the plunger and the barrel. An abraded surface 44 is located on the tip end 40 positioned to engage the barrel abraded surface 32. In the preferred embodiment, the abraded surface 44 is serrated and the sealing gland 42 is preferably integral with the plunger abraded surface 44. A cavity or space 45 is defined within the barrel 22 between the abraded surfaces 32 and 44, and the aperture 34 creates a fluid connection between catheter 26 and cavity 45.

The plunger 24 is removable from the barrel 22 to allow medication, preferably a pill (not shown), to be placed in the barrel. The plunger is also adapted to rotate within the barrel to assist in grinding the pill between abraded surfaces 32 and 44. The barrel 22 and the plunger 24 may include a threaded fitting 47 which advances the plunger into the barrel as the plunger is rotated therein (see FIGS. 2 and 5). The threaded fitting creates a positive grinding action between the abraded surfaces 32 and 44 as the plunger is rotated within the barrel.

The seal created by sealing gland 42 allows liquid to be drawn into the barrel by withdrawing the plunger from the barrel as the catheter tip 27 is submerged in a container of water or the like. The barrel may then be flushed, and the suspension comprising the crushed pill and water evacuated from the syringe, by advancing the plunger into the barrel thereby forcing the suspension through the catheter.

Figure 5:
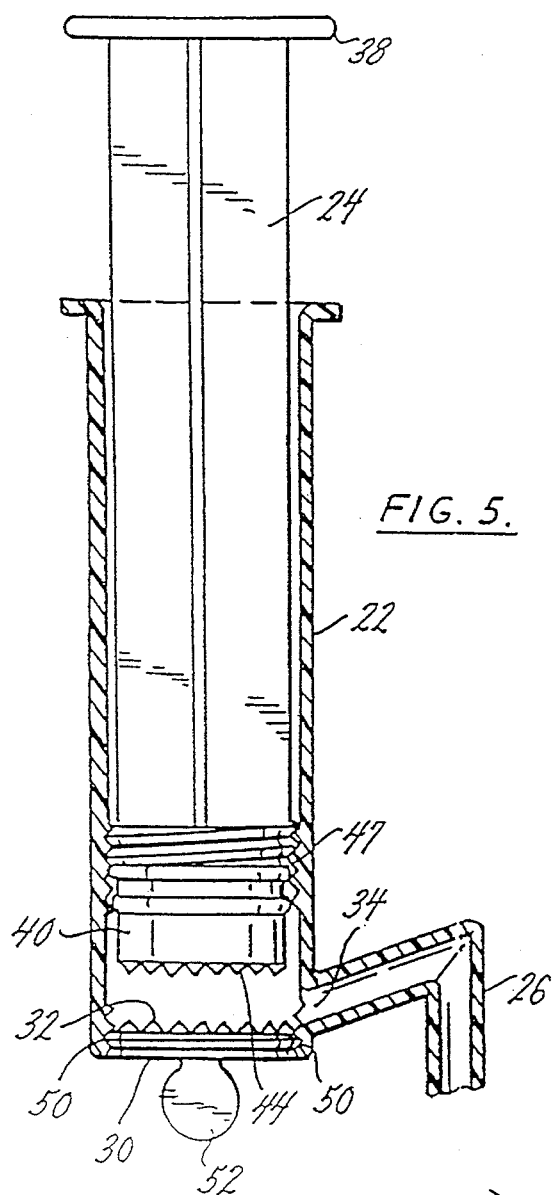
FIG. 5 is a cross-sectional view of the closed bottom constructed according to an alternative embodiment of the invention disclosed in the parent permitting the bottom to be rotated relative to the syringe barrel and plunger.

In an alternative embodiment disclosed in the parent, the closed end 30 is screw thread fastened to the barrel 22 by threaded grooves 50 (see FIG. 5). The closed end 30 is thereby rotatable with respect to the rest of barrel 22 and is removable. The closed end 30 may comprise a thumb screw 52, for example. In this embodiment, the pill may be placed in the barrel 22 by removing the closed end 30 and the closed end may be rotated to facilitate crushing and grinding the pill.

Figure 6:
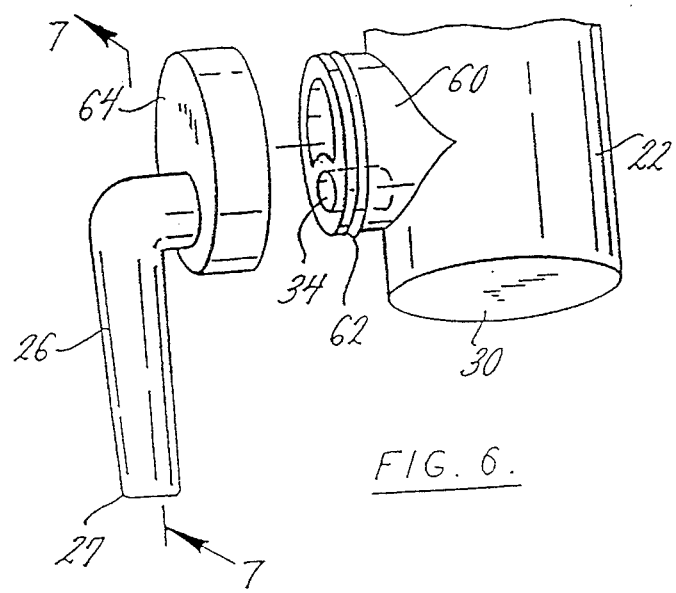
FIG. 6 is an exploded isometric view of a second alternative embodiment of the invention disclosed in the parent illustrating the catheter and cap from the stub housing.

According to a second alternative embodiment disclosed in the parent, the syringe 20 includes means for adjustably sealing the fluid connection between catheter 26 and cavity 45. The adjustable sealing means allows liquid to be temporarily trapped within the cavity. One example of the adjustable sealing means is illustrated in FIG. 6. The barrel 22 further includes a stub housing 60 extending radially, and non-concentrically, from aperture 34, and a retaining lip 62 extends around the outside surface of the stub housing. The aperture 34 extends through the stub housing 60.

Figure 7:
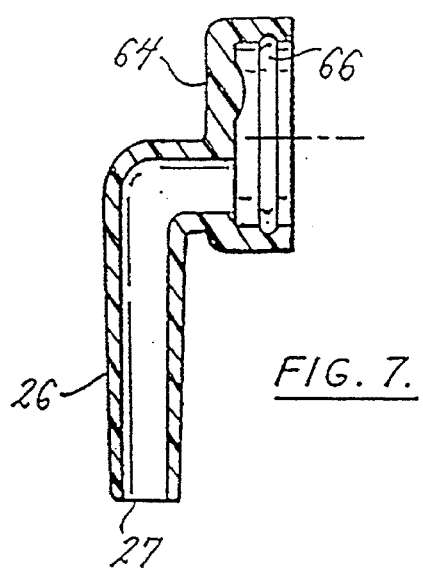
FIG. 7 is a cross-sectional view taken along lines 7—7 in FIG. 6 detailing the catheter position relative to the cap and the groove within the cap.

Catheter 26 includes a cap 64 rotatably coupled to the stub housing and extending radially, and non-concentrically, from the catheter end opposite tip 27. The cap 64 includes a groove 66 (see FIG. 7) appropriately sized to mate with retaining lip 62 thereby creating a liquid-tight seal between the cap and stub housing. The cap 64, being rotatable about the stub housing axis, may be rotated to align the catheter and the aperture for fluid connection, or to misalign the catheter and aperture to seal the connection.

Figure 8:
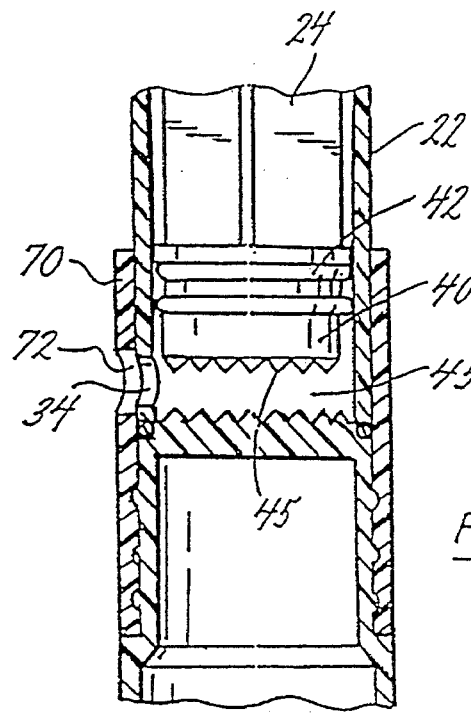
FIG. 8 is a cross-sectional view of a third alternative embodiment of the invention disclosed in the parent illustrating the collar and collar aperture of the adjustable sealing means.

Another example of the adjustable sealing means is illustrated in FIG. 8. A collar 70, having a collar aperture 72, is fitted around the barrel 22 in a substantially fluid tight relationship. The collar 70 is rotatable about the barrel axis and may alternately be rotated to align the collar aperture 72 with the barrel aperture 34, creating a fluid connection therebetween, or to seal the apertures 34 and 72 from each other.

According to the method of the invention disclosed in the parent, the plunger 24 is removed from the barrel 22 and medication, preferably a pill (not shown), is placed in the barrel. The plunger is advanced into the barrel until the pill is lodged snugly between the abraded surfaces 32 and 44. The plunger 24 is then rotated as pressure is exerted thereon and against the pill thereby rotating abraded surface 44 with respect to abraded surface 32 until the pill is crushed and/or ground into a powder 48. The tip 27 of catheter 26 is placed in a liquid, a glass of water for example, and the plunger 24 is withdrawn from the barrel thereby drawing liquid into the barrel cavity 45 to mix with the powder 48 of the crushed pill. The catheter 27 has a crook 29 formed therein to inhibit the free flow of liquid out of the catheter after it is withdrawn from the glass. This helps prevent any of the suspended pill particles from escaping. The syringe 20 may then be shaken to dislodge any powder residue off the abraded surfaces 32 and 44. During shaking, it may be desirable to close off the end of tip 27 to prevent any of the suspension from escaping. The tip 27 of catheter 26 is then inserted into tube 36 and the suspension within the barrel is flushed from the syringe by advancing the plunger into the barrel.

According to an alternative embodiment of the method disclosed in the parent the pill may be placed into the barrel 24 by unscrewing and removing the closed end 30 (see FIG. 5), placing the pill into the barrel, and replacing the closed end. The plunger is then advanced into the barrel until the pill is squeezed snugly between abraded surfaces 32 and 44. The pill may be crushed and/or ground by twisting the closed end 30 within the threaded grooves 50 to thereby rotate abraded surface 32 with respect to abraded surface 44. Further, the barrel 22 can be held steady while simultaneously rotating the plunger within the barrel and twisting the closed end 30 within the threaded grooves 50. This technique provides relative motion between both of the abraded surfaces and the barrel, thereby intensifying the grinding action.

According to a second alternative embodiment of the method disclosed in the parent, once the liquid is drawn into cavity 45 to mix with powder 48, the fluid connection between the catheter 26 and the cavity 45 is temporarily sealed. This allows the syringe to be shaken, violently if necessary, without the possibility of losing liquid or medication from the syringe. Once the powder is fully suspended in the liquid, the catheter-cavity fluid seal is restored and the suspension is flushed from the syringe by advancing the plunger into the barrel.

While the medication placed in the barrel 22 is preferably a pill, the term pill is intended to include tablets, capsules, and other discrete units of medication. The pill may also include particles, powder, or liquid forms of medication. For instance, a capsule may be provided which houses medication within a shell. The medication may be placed in the barrel by holding the capsule over the open end 28 of the barrel and breaking the capsule shell thereby dropping the medication into the barrel. If the form of medication is not readily suspended in water, the syringe 20 crushes and/or grinds the medication as disclosed above.

It is understood that the above-described pill crushing method may be practiced without administering the dosage through the catheter into a tube. Alternatively, the suspension may be delivered to a tissue site, for example, or elsewhere as needed or desired.

It is further understood that the syringe 20 may be intended for single use application, made of plastic or other suitable disposable material, and disposed of after one usage to eliminate cross-contamination. Further, the syringe may comprise an electric pill crusher with removable plastic inserts or surfaces for the plunger, barrel, and/or catheter, the removable plastic inserts being replaceable for single use application. In this variation, the plunger can be electrically advanced and rotated to crush the pill, withdrawn to mix the suspension, and even advanced a second time to administer.

Figure 9:
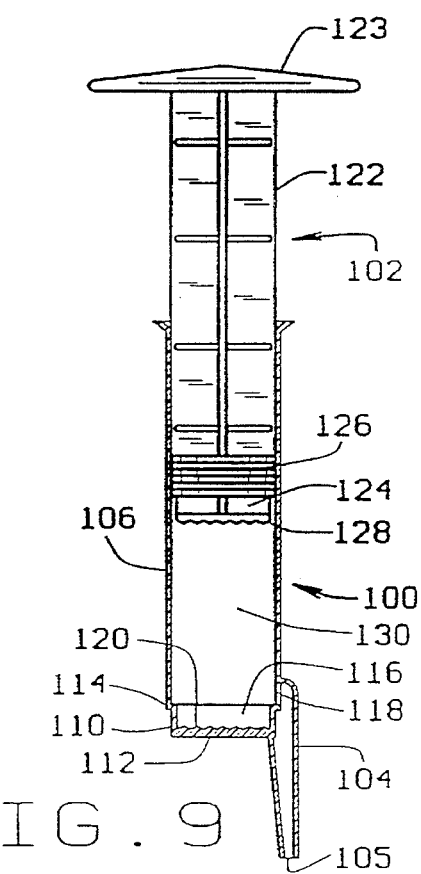
FIG. 9 is a cross-sectional view of the pill crushing syringe of the continuation-in-part to the parent application illustrating the bi-level barrel, the bi-level plunger and the substantially straight side mounted catheter.

Building on the invention disclosed above, the inventors improved on their earlier pill crushing syringe by providing a syringe including a bi-level barrel 100, a mating bi-level plunger 102, and a substantially straight side mounted catheter 104 oriented substantially parallel to barrel 100 and having a tip end 105 (see FIG. 9) extending beyond closed end 112. The term "bi-level barrel" shall herein refer to a barrel having a first or standard interior diameter section 106, a reduced interior diameter section 110 having a closed end 112, a transition 114 between the first diameter section 106 and the reduced diameter section 110, and with a pocket 116 being thereby formed between the closed end 112 and the transition 114. In the preferred embodiment, an aperture 118 is formed through the first diameter section 106 and adjacent the transition 114, and the catheter 104 is connected around and extends from the aperture 118. Both sections 106 and 110 of the bi-level barrel 100 preferably have a cylindrical wall, and an abraded surface 120 is preferably located on the closed end 112.

The term "bi-level plunger" shall herein refer to a plunger having a first or standard exterior diameter section 122 with a handle 123, a reduced exterior diameter tip section 124 and a sealing gland 126 on the first diameter section 122 providing an air-tight relationship between the plunger 102 and the barrel 100. Although shown on plunger 102, the sealing gland 126 may instead be formed in barrel 100, or as part of both. In the preferred embodiment, the reduced diameter tip section 124 includes an abraded surface 128 positioned to engage the barrel abraded surface 120 as the plunger is advanced within the barrel. A cavity or space 130 is defined within the barrel 100 between the abraded surfaces 120 and 128, and the aperture 118 creates a fluid connection between the cavity 130 and the catheter 104.

The bi-level barrel 100 and the bi-level plunger 102 are adapted to allow the plunger tip section 124 to mate with and rotate within the barrel pocket 116 such that a pill may be crushed and/or ground between the abraded surfaces 120 and 128. In the preferred embodiment, the handle 123 is appropriately sized to allow a typical human hand to develop sufficient torque about the plunger axis to easily grind the pill between the abraded surfaces 120 and 128. The barrel and plunger may also include a threaded fitting (similar to the threaded fitting 47 shown in FIG. 2) to create a positive grinding action as the plunger is advanced by being rotated within the barrel.

In operation, the plunger 102 is removed from the barrel 100 to allow medication, preferably a pill (not shown), to be placed within the barrel, the plunger is advanced and rotated in the barrel lodging the pill between the abraded surfaces 120 and 128 and facilitating crushing and grinding of the pill into a powder. Holding the syringe substantially upright ensures that the powder (pill crushings) remains in the pocket 116 which is below the aperture 118 in this arrangement. This prevents the medication from escaping the barrel via the catheter 104 prior to aspiration. While the preferred embodiment includes the pocket 116 within bi-level barrel 100, it is understood that the pocket is not essential to maintaining high dosage integrity. In this embodiment, spacing the aperture 118 from the closed barrel end 112 prevents the pill crushings from escaping through the catheter 104 prior to aspiration. The sealing gland 126 allows a liquid to be drawn into the barrel 100 by withdrawing the plunger 102 from the barrel as the catheter tip 105 is submerged in a liquid. If desired, the syringe may be shaken to further mix the suspension. The barrel may then be flushed, and the suspension comprising the crushed pill and the liquid evacuated from the syringe by advancing the plunger into the barrel thereby forcing the suspension through the catheter.

Figure 10:
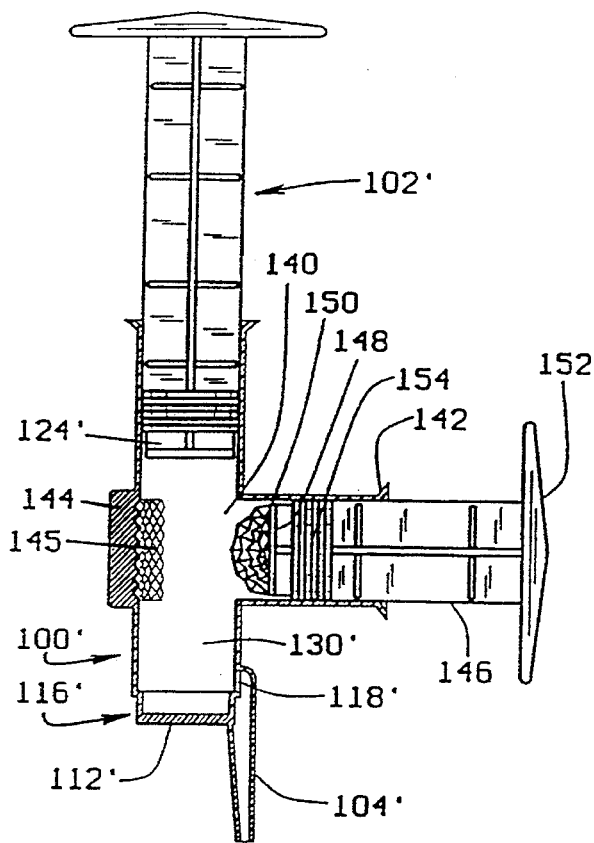
FIG. 10 is a cross-sectional view of an alternative embodiment of the continuation-in-part illustrating the barrel having a side entry plunger.
Figure 12:
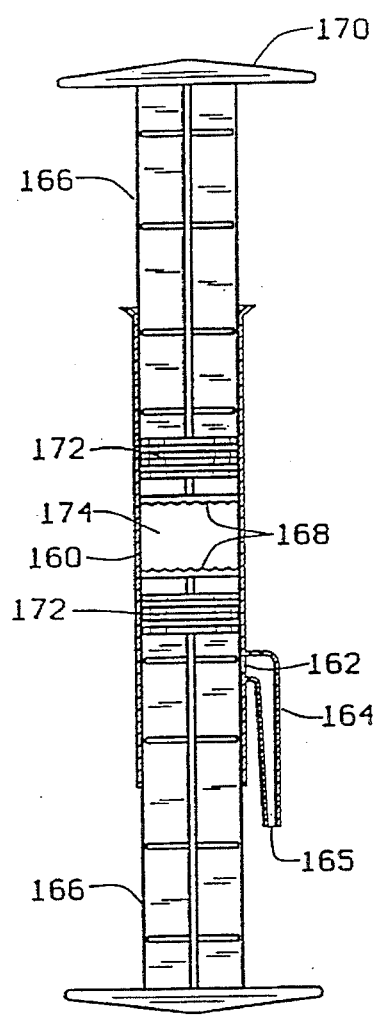
FIG. 12 is a cross-sectional view of another alternative embodiment of the continuation-in-part illustrating a double barrel syringe.

An alternative embodiment of the invention disclosed in the continuation-in-part is illustrated in FIG. 10 and includes a bi-level barrel 100' having a closed end 112', a pocket 116' ahd an aperture 118' adjacent the pocket, a catheter 104' connected around and extending from the aperture 118', and a mating bi-level plunger 102'. A space or cavity 130' is defined within the barrel 100' between the plunger 102' and the closed end 112'. The bi-level barrel 100' further includes a side opening 140, a hollow side arm 142, and a reinforced barrel wall section 144 opposite the side opening 140. The reinforced barrel wall section 144 includes an interior abraded surface 145 which generally conforms to the shape of the barrel wall, allowing the plunger 102' to pass thereby. A side entry plunger 146 is movable within the side arm 142 and includes a tip end 148 having a convex abraded surface 150 thereon, a handle end 152, and may include a sealing gland 154. The abraded surface 145 is shaped and positioned to engage the convex side entry plunger abraded surface 150.

In operation, a pill is inserted into the barrel 100' by removing the plunger 102' or the side entry plunger 146. The plunger 102' is positioned to allow the side entry plunger 146 access to the cavity 130'. The syringe may then, if not already, be oriented horizontally. The pill is positioned between the side entry plunger 146 and the abraded surface 145, the side entry plunger 146 is advanced into the cavity 130' and may be rotated therein to thereby crush and/or grind the pill into a powder between the abraded surfaces 145 and 150. The side entry plunger 146 is then withdrawn from within the cavity 130' but is preferably not removed from the side arm 142. The syringe is then re-oriented substantially upright thereby causing the crushed pill ingredients to drop into the pocket 116'. The syringe may be lightly tapped to dislodge pill crushings remaining on the abraded surface 145. The bi-level plunger 102' is gently advanced completely into the barrel 100' to avoid blowing the pill crushings out through the catheter 104' and aspiration is performed substantially as explained above. Alternatively, the side entry plunger 146 may be used to aspirate the cavity 130'.

As illustrated in FIG. 10, the plunger 102' and barrel closed end 112' preferably do not have abraded surfaces in this embodiment. However, an abraded surface may be added to the plunger 102' and/or closed end 112' to assist in further crushing or grinding the pill ingredients deposited in the pocket 116' prior to aspiration. Also, these abraded surfaces can be used to crush a pill if desired. Threaded fittings may be included between the plunger 102' and the barrel 100' and/or the side entry plunger 146 and the side arm 142 to create a more positive grinding action as the plunger 102' or 146 is rotated. The threaded fittings in this embodiment are preferably similar to the threaded fitting 47 shown in FIG. 2.

Figure 11:
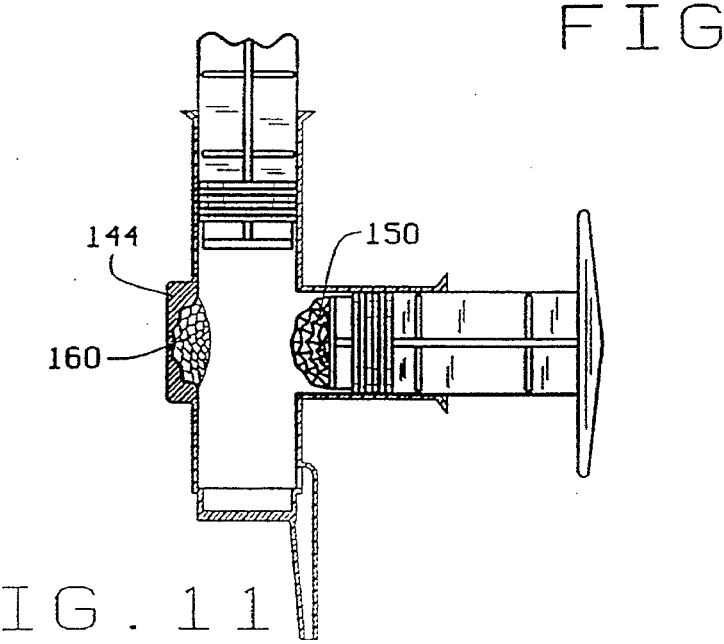
FIG. 11 is a cross-sectional view of a variation of the alternative embodiment shown in FIG. 10 illustrating a concave interior abraded surface opposite the side entry plunger.

A variation of this embodiment incorporates a concave interior abraded surface 160 (see FIG. 11). The concave abraded surface 160 is shaped, sized, and positioned to closely engage the convex side entry plunger abraded surface 150. This relationship assists in centering the pill between the abraded surfaces 150 and 160 and achieving a more thorough crushing of the pill.

Another alternative embodiment is illustrated in FIG. 11. This embodiment provides a cylinder 160 having an aperture 162 through the cylinder wall and a catheter 164 connected around and extending from the aperture 162. The catheter 164 includes a tip end 165. Two plungers 166 having opposing abraded tip ends 168 are movable and rotatable within the cylinder 160. Each plunger 166 includes a handle 170 and a sealing gland 172. The sealing glands create a substantially air-tight relationship between the plungers 166 and the cylinder 160. A cavity or space 174 is defined within the cylinder 160 between the opposed abraded tip ends 168.

In operation, one of the plungers 166 is removed from the cylinder 160 and a pill is placed therein. The plunger is placed back into the cylinder and both plungers are preferably advanced toward one another within the cylinder such that the pill is positioned adjacent both abraded tip ends 168 while the space 174 is not aligned with the aperture 162. To facilitate plunger movement, aperture 162 may be kept in communication with space 174 until just before the pill is crushed. The plungers 166 are next rotated and pushed further together thereby crushing and grinding the pill into a powder. The plungers are simultaneously moved within the syringe until the space 174 is in fluid communication with the aperture 162. To minimize loss of pill crushings, space 174 may be oriented just out of communication with aperture 162 to thereby minimize the distance for travel by the two plungers in order to re-establish communication. At this point, the plungers are preferably as close together as possible. One or both of the plungers is then gently pulled away from the other while the catheter tip 165 is submerged in a liquid thereby drawing the liquid into the cylinder 160 and suspending the pill crushings in the liquid. The syringe is then positioned as desired for administering the pill and the suspension may then be flushed from the cylinder by advancing one or both of the plungers toward the other.

Figure 13:
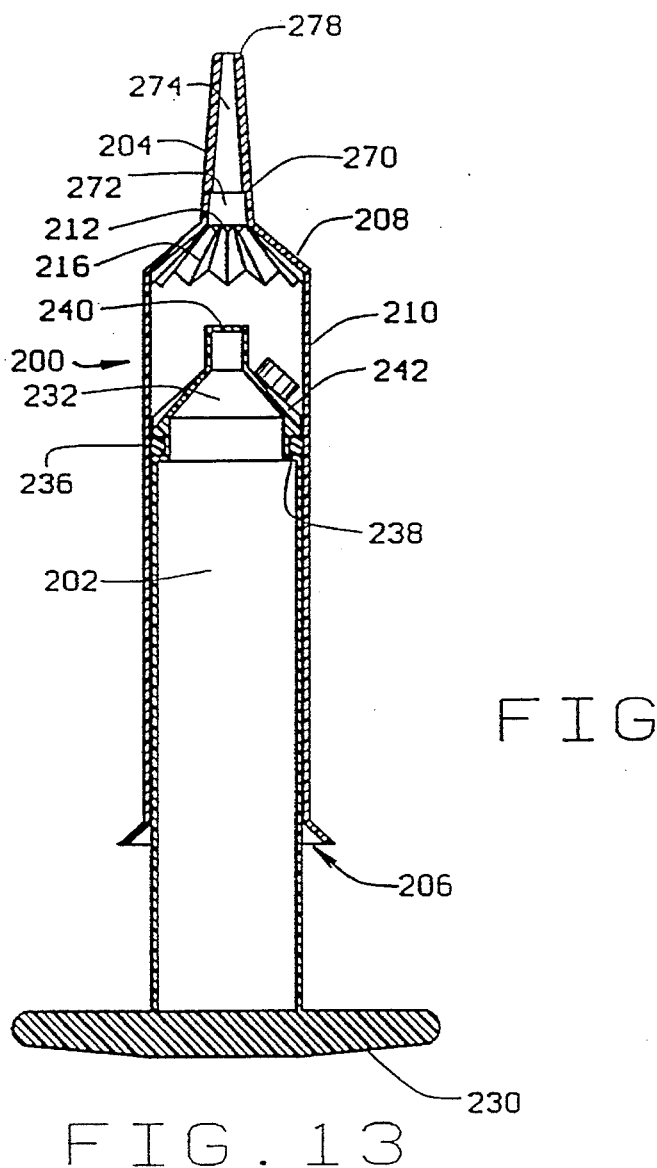
FIG. 13 is a cross-sectional view of the pill crushing syringe constructed according to the principles of the present invention illustrating the plunger, the barrel, and the axially aligned catheter as well as the pill location when the syringe is in an inverted vertical orientation.
Figure 14:
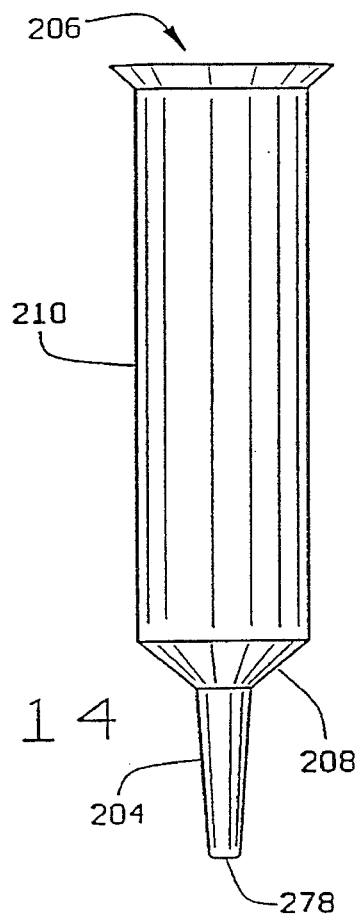
FIG. 14 is side view of the barrel of the present invention illustrating the catheter extending from the barrel second end.
Figure 15:
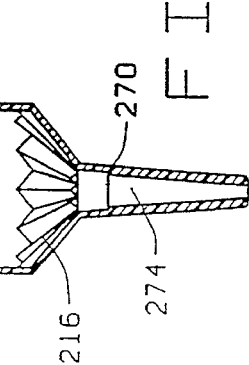
FIG. 15 is a cross-sectional view of the barrel in FIG. 10 illustrating the abraded surface pattern on the second barrel end.
Figure 16:
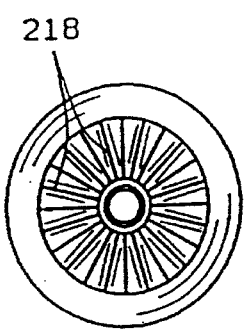
FIG. 16 is an axial view into the barrel of FIG. 10.

Building on the invention disclosed above, the inventors have improved on their earlier pill crushing syringe by providing a syringe as shown in FIG. 13 including a barrel 200, a plunger 202, and a substantially straight axially aligned catheter 204. The barrel includes a first open end 206, a second end 208, and a cylindrical wall 210 forming an interior therebetween. The second end 208 is preferably frustoconically shaped with an aperture 212 at its apex. The catheter 204 is connected around and extends from the aperture 212 in visual conformity with typical syringes used in the health care field. The second end 208 preferably includes an abraded surface 216, and the abraded surface 216 preferably includes a pattern of radial protrusions 218 as shown in FIGS. 13, 15, and 16. As used herein the term "radial" shall mean a pattern of protrusions arranged about a central point on a flat surface or arranged about an apex on a conic or frustoconic surface.

Figure 18:
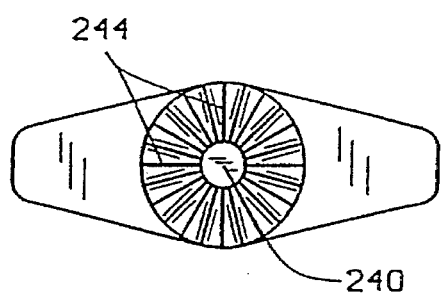
FIG. 18 is an axial view of the plunger taken along lines 18—18 in FIG. 17.
Figure 17:
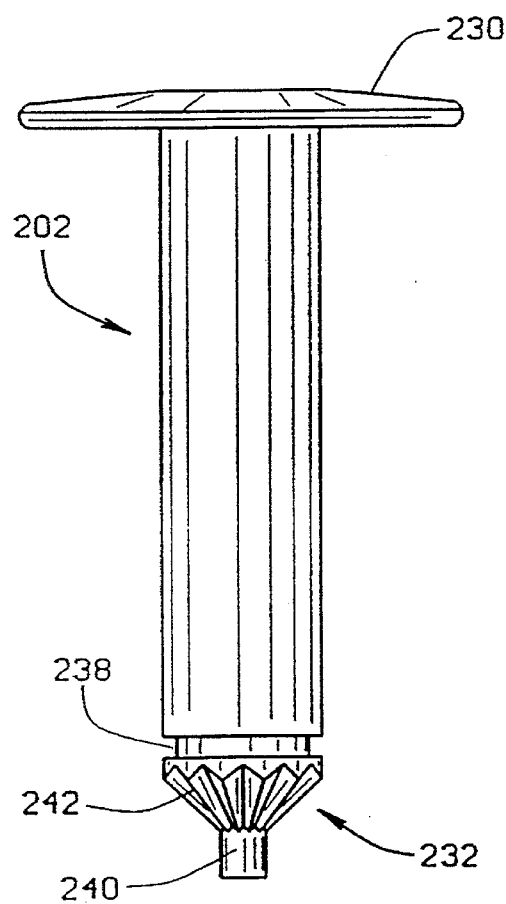
FIG. 17 is a side view of the plunger of the present invention illustrating the radial protrusion pattern on the plunger tip, the plug extending therefrom, and the O-ring seat positioned adjacent the tip.

The plunger 202 includes a handle end 230, a preferably conically shaped tip end 232, and a sealing gland 234, including an O-ring 236 housed within an O-ring seat 238. The tip end preferably includes a plug 240 at the apex thereof and an abraded surface 242 around the plug 240 as shown in FIGS. 17 and 18. In the preferred embodiment, the plunger abraded surface 242 includes a pattern of radial protrusions 244 which resembles the protrusion pattern of the barrel abraded surface 216.

Figure 19:
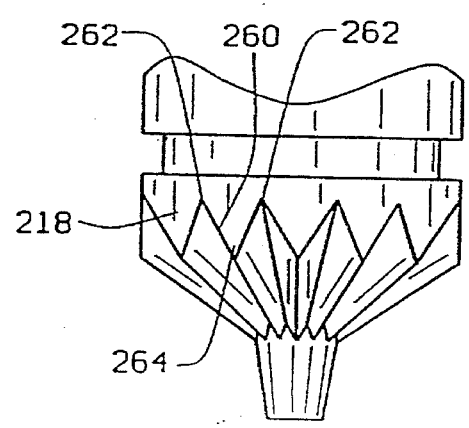
FIG. 19 is an enlarged side view detailing the abraded surface and plug of the plunger tip.

As illustrated in FIG. 19, each radial protrusion 218 on the plunger tip in the preferred embodiment includes two substantially straight walls 260 starting at two bases 262 and meeting at a ridge 264. The ridges 264 are preferably spaced 30° apart about the circumference of the plunger with the bases 262 equidistant therebetween and the ridges 264 are preferably inclined at approximately a 25° angle with respect to a plane orthogonal to the plunger axis. The bases 262 are joined to form a plurality of valleys which preferably inclined at approximately a 36° angle with respect to a plane orthogonal to the plunger axis. The radial protrusions 218 of the barrel second end mirror the above described plunger radial protrusion pattern 244. In other words, the ridges and valleys of radial protrusions 218 are aligned at the same angles as radial protrusions 244. See FIGS. 15, 16, and 20. Thus, each of the radially extending protrusions form a series of alternating ridges and valleys.

Figure 20:
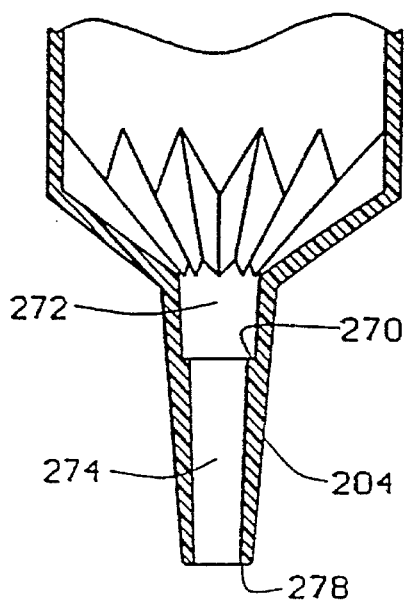
FIG. 20 is an enlarged side view detailing the abraded surface of the barrel and the catheter lip.
Figure 21:
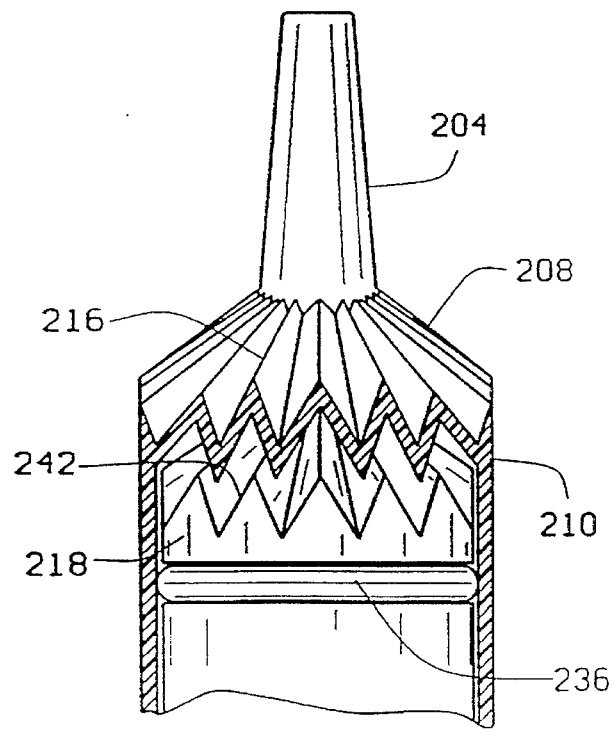
FIG. 21 is a partial side view of the syringe with the barrel side wall broken away to illustrate the opposing abraded surfaces spaced apart when the plunger is fully inserted into the barrel.

As illustrated in FIGS. 13 and 20, the catheter 204 includes a lip 270 therein marking an abrupt narrowing of the catheter chamber which otherwise gradually tapers from a larger diameter section 272 to a smaller diameter section 274 at a tip 278 of the catheter. The plug 240 fits snugly within the larger diameter catheter section 272 and rests against the lip 270 when the plunger is fully advanced within the barrel. In the preferred embodiment, the plug 240 meets the lip 270 before the abraded surfaces 216 and 242 are able to "mesh" as shown in FIG. 21. As used herein, the term "mesh" shall mean an arrangement where the ridges 264 of either abraded surface 216 or 242 rest flush against the valleys 262 of its opposing abraded surface when no pill is positioned therebetween.

The opposing abraded surfaces 216 and 242 are coaxially aligned which facilitates reliable alignment of the opposing ridges and valleys of the radial protrusion patterns 218 and 244. While the plug 240 in the preferred embodiment prohibits the opposing abraded surfaces 216 and 242 from meshing, a portion of the inclined surface nearest the top of the ridges 264 preferably contact one another when the plunger is fully advanced into the barrel and rotated. This allows the opposing protrusions 218 and 244 to partially wipe each other when the plunger is rotated within the barrel helping to remove any pill crushings which might otherwise be matted against the protrusion walls 260 and creating a vibrating reciprocating action which aids in more completely crushing the pill. The vibration is caused by the inclined surfaces contacting each other and the reciprocation is caused by the surfaces riding up and over each other as the plunger is rotated in the barrel. The portion of each protrusion wall 260 which is wiped and the degree of vibrating reciprocation is readily predictable and easily adjusted by, inter alia, altering the length of plug 240. As the two sets of radial protrusions "mirror" each other, a surface area generally in the shape of a rectangle "wipes" as they first contact. However, this "wiping area" can also be adjusted by changing the shape, size, or orientation of one set of radial protrusions with respect to the other. Furthermore, prohibiting the abraded surfaces from meshing minimizes packing of the pill crushings into a cake within the valleys of opposing abraded surfaces. The crushed powder which falls into the valleys is not contacted by a ridge of the opposing surface and instead is isolated from further abrasive action.

In operation, one or more pills are placed within the barrel 200 and the plunger 202 is advanced slightly into the barrel thereby trapping the pill(s) within the barrel interior. See FIG. 13. The syringe is positioned in a substantially inverted vertical orientation such that the catheter tip 278 is pointing substantially upward. As illustrated in FIG. 13, because the plunger tip end 232 is conically shaped, positioning the syringe in its inverted vertical orientation causes the pill to gravitate away from the aperture 212. The plunger is advanced into the barrel until the pill is lodged snugly between the abraded surfaces 216 and 242. The plunger 202 is then rotated as pressure is exerted thereon and against the pill thereby rotating abraded surface 216 with respect to abraded surface 242 until the pill is crushed and/or ground into a powder. In the preferred embodiment, the plunger handle end 230 is appropriately sized to allow a typical human hand to develop sufficient torque about the plunger axis to easily grind the pill between the abraded surfaces 216 and 242. The barrel and plunger may also include a threaded fitting (similar to the threaded fitting 47 shown in FIG. 2) to create a positive grinding action as the plunger is advanced by being rotated within the barrel.

In the preferred embodiment the outer circumference of the plunger abraded surface and the inner and outer circumferences of the barrel abraded surface are rounded or chamfered. Experimentation has shown that so rounding or chamfering minimizes packing of the pill particles thereabout.

The sealing gland 234 is preferably located adjacent the plunger tip end 232 as illustrated in FIG. 13. The sealing gland 234 assists in the aspiration stage by maintaining an airtight seal so that liquid is drawn into the barrel by withdrawing the plunger from the barrel as the catheter tip 278 is submerged in a container of water or the like. By positioning the sealing gland adjacent the plunger tip end 232, the sealing gland in the present invention also advances the goal of high dosage compliance and integrity by trapping any pill particles which might migrate down the barrel wall 210 as the plunger is advanced and rotated therein with the syringe in its inverted vertical orientation. These pill particles would likely become exposed and mixed with the liquid as the plunger is withdrawn during aspiration.

When the pill(s) is sufficiently crushed, the plug 240 is pushed snugly against the catheter lip 270 thereby blocking the catheter passage and minimizing the risk of any crushed pill ingredients prematurely escaping through the catheter as the syringe is moved from its inverted vertical orientation. In an alternate construction, the plug 240 will interference fit into the catheter to limit the advance of the plunger into the barrel. The plunger 202 is preferably fully advanced within the barrel 200 until after the catheter tip 278 is submerged in the desired liquid. By withdrawing the plunger 202 from the barrel 200 at this time, the liquid is drawn into the syringe and mixed with the pill crushings conveniently forming a suspension of pill crushings. To flush the suspension out of the syringe the plunger is simply advanced back into the barrel. The frustoconic shape of the barrel second end further contributes to the high dosage compliance of the present invention by allowing any remaining liquid to gravity flow out of the syringe thereby minimizing any residue within the syringe.

To further emphasize what is implicit in the parent hereto, as cross-referenced above, the term "pill" as used herein includes tablets, capsules, and other discrete units of medication, cooking herbs, spices, and similar solids. The pill may also include particles, powder, or liquid forms of medication, cooking herbs, spices, or similar substances. Moreover, while the preferred embodiment describes administering the suspension by forcing the suspension through the catheter and into a tube attached to a patient, it is understood that the invention may be practiced without administering the suspension through a tube. For instance, the suspension may be administered orally, rectally, delivered to a tissue site, or used in basting or other types of food preparation. Further, the invention is applicable to both human and veterinary applications (i.e. the suspension may be administered directly from the catheter into the mouth of an animal).

Although illustrated embodiments of the present invention are described herein with reference to the accompanying drawings, it is to be understood that the invention is not limited to those precise embodiments and that various other changes and modifications may be made by one skilled in the art without departing from the scope or spirit of the invention. The scope of the invention is defined solely by the claims, and their equivalents.

What is claimed is:

1. A pill crushing syringe comprising a barrel with an axially aligned catheter mounted thereto, a plunger moveable within said barrel, and at least one abraded surface within said syringe so that a pill placed within said syringe is crushed by the abraded surface as the plunger is moved within the syringe.

2. The pill crushing syringe of claim 1 wherein the barrel includes at least one abraded surface and the plunger includes at least one abraded surface.

3. The pill crushing syringe of claim 2 wherein said abraded surfaces are coaxially aligned to thereby facilitate proper alignment of said abraded surfaces.

4. The pill crushing syringe of claim 3 wherein each of said abraded surfaces includes a radially extending protrusion pattern.

5. The pill crushing syringe of claim 4 wherein said radial protrusion pattern includes a plurality of alternating ridges and valleys.

6. The pill crushing syringe of claim 5 further including means for limiting the advance of said plunger into said barrel to thereby prevent said abraded surfaces from meshing.

7. The pill crushing syringe of claim 6 wherein said plunger limiting means includes means for limiting the advance of said plunger to a point where said abraded surfaces contact each other as said plunger is rotated in said barrel.

8. The pill crushing syringe of claim 7 wherein the abraded surfaces are aligned with respect to each other so that they wipe against each other as the plunger reaches said point and is rotated within the barrel.

9. The pill crushing syringe of claim 8 wherein said plunger limiting means includes a plug extending from a tip end of said plunger.

10. The pill crushing syringe of claim 9 wherein the plunger limiting means further includes a lip in said catheter for mating with said plug as the plunger is advanced into the barrel.

11. In a pill crushing syringe comprising a barrel, a plunger moveable within said barrel, and at least one abraded surface within said syringe so that a pill placed within said syringe and adjacent said abraded surface is crushed as said plunger is moved within the barrel, the improvement comprising said abraded surface having a radially extending protrusion pattern so that any pill crushings created from crushing said pill are free to migrate in a radial direction.

12. The pill crushing syringe of claim 11 further comprising a pair of matching abraded surfaces, said abraded surfaces being located in said syringe so that a pill is captured therebetween as said plunger is advanced into the barrel.

13. The pill crushing syringe of claim 12 further comprising means for spacing said abraded surfaces to thereby prevent meshing of said abraded surfaces as a pill is crushed.

14. The pill crushing syringe of claim 13 wherein said syringe includes a generally axially aligned catheter extending from said barrel and said spacing means includes a generally axially aligned plug extending from said plunger, said plug and catheter being substantially aligned with each other so that said plug moves into said catheter as said plunger is advanced into the barrel to thereby limit further advancement thereof into the barrel.

15. The pill crushing syringe of claim 14 wherein each abraded surface is comprised of a plurality of radially extending ridges and valleys.

16. The pill crushing syringe of claim 15 wherein the abraded surfaces are coaxially aligned.

17. In a pill crushing syringe comprising a barrel, a plunger moveable within the barrel, and each of the barrel and the plunger having included thereon one of a pair of opposing abraded surfaces so that as the plunger is advanced within the barrel the abraded surfaces squeeze a pill placed therebetween to thereby crush it, the improvement including means for preventing said opposing abraded surfaces from meshing as the plunger is advanced within the barrel.

18. The pill crushing syringe of claim 17 wherein said meshing preventing means comprises a plug extending from the plunger abraded surface.

19. The pill crushing syringe of claim 18 wherein said abraded surfaces are aligned to wipe against each other as said plunger is rotated within the barrel.

20. The pill crushing syringe of claim 19 wherein said plug is axially aligned.

21. The pill crushing syringe of claim 20 wherein the syringe includes an axial aligned catheter extending from the barrel, the plug and catheter being substantially aligned with each other so that the plug moves into the catheter as the plunger is advanced into the barrel.

22. The pill crushing syringe of claim 21 wherein the meshing preventing means includes a lip for mating with the plug to thereby limit further advancement of the plug into the catheter and thereby limit further advancement of the plunger into the barrel.

23. A pill crushing syringe including:

a barrel having a first open end, a second end, and a wall therebetween defining a barrel interior;

a catheter in communication with the barrel interior by an aperture therethrough;

a plunger moveable within said barrel;

at least one abraded surface within said syringe so that a pill placed within the syringe and adjacent the abraded surface is crushed as said plunger is moved within the barrel; and a tip end of said plunger being non-orthogonal relative to the plunger axis such that a pill placed within the barrel interior is forced by gravity away from the aperture when the syringe is in an inverted vertical orientation to thereby impede pill particles from entering the catheter as said pill is crushed by the inverted vertically oriented syringe.

24. The pill crushing syringe of claim 23 wherein the barrel second end is non-orthogonal relative to the barrel axis and the aperture is positioned such that fluid within the barrel interior gravity flows toward the aperture when the catheter is pointing downward to thereby minimize fluid residue within the syringe.

25. The pill crushing syringe of claim 24 wherein the plunger tip end is conical and the barrel second end forms a frustoconical shape around the aperture.

26. The pill crushing syringe of claim 25 further including a plug extending from the apex of said plunger tip for mating with a lip within the catheter to thereby impeded pill particles from prematurely entering the catheter when the plunger is fully advanced into the barrel.

27. A pill crushing syringe comprising:

a barrel having an open end, a frustoconic second end with an axially aligned catheter mounted around an aperture through an apex thereof;

a plunger with a conic tip end; and a pair of opposing abraded surfaces on each of the barrel second end and the plunger tip end such that a pill placed within the syringe is crushed therebetween as the plunger is moved within the barrel.

28. The pill crushing syringe of claim 27 further comprising a plug extending axially from the apex of the plunger tip end, the plug and catheter being substantially aligned with each other so that said plug moves into said catheter as the plunger is advanced into the barrel to thereby prevent said opposing abraded surfaces from meshing by limit further advancement of the plunger into the barrel prior thereto.

29. The pill crushing syringe of claim 28 wherein said catheter includes a lip for mating with the plug to thereby impede any pill crushings created from crushing said pill from escaping through said catheter when the plunger is fully advanced into the barrel.

30. A method of creating a suspension of pill crushing in a syringe comprising the steps of:

placing a pill into a barrel of the syringe, said barrel having a catheter in fluid communication therewith;

advancing a plunger within the barrel to bring at least one abraded surface into contact with the pill to thereby crush the pill against said abraded surface;

blocking said catheter with a plug on the plunger as the plunger is advanced within the barrel to thereby impede pill crushings from prematurely entering the catheter; and drawing liquid into the barrel by withdrawing the plunger from within the barrel as a tip end of said catheter is submerged in a liquid to thereby suspend said pill crushings in the liquid.

31. The method according to claim 30 wherein the plunger includes a conic tip end and said fluid communication is centered at an end of said barrel, and the step of advancing the plunger within the barrel includes the step of positioning the syringe in an inverted vertical orientation so that said conic plunger tip guides the pill away from said catheter.

32. The method according to claim 30 further comprising the step of flushing the suspension out of the syringe by advancing the plunger within the syringe.

33. The method according to claim 32 wherein the barrel second end is frustoconically shaped with said fluid communication at the center thereof and the flushing step includes the step of positioning said catheter substantially downward thereby enabling said suspension to gravity flow out of said syringe and minimizing any residue therein.

34. The method according to claim 33 wherein the step of advancing the plunger includes the step of rotating the plunger with the barrel to facilitate grinding the pill into smaller pieces.

35. A method of creating a suspension of pill crushings in a syringe comprising the steps of:

placing a pill into a barrel of the syringe, said barrel having a catheter in fluid communication therewith;

advancing a plunger within the barrel to bring a pair of abraded surfaces into contact with the pill to thereby crush the pill between said abraded surfaces;

limiting the advance of said plunger within the barrel to prevent meshing of said abraded surfaces; and drawing liquid into the barrel by withdrawing the plunger from within the barrel as a tip end of said catheter is submerged in a liquid to thereby suspend said pill crushings in the liquid.

36. The method according to claim 35 wherein the step of limiting the advance of said plunger includes the step of limiting the advance of said plunger to a point at which said abraded surfaces intermittently contact each other as the plunger is rotated within the barrel.

* * * * *